United States Patent

Vara et al.

[11] Patent Number: 5,094,917
[45] Date of Patent: Mar. 10, 1992

[54] ALK-1-ENYL ETHER SILICATES

[75] Inventors: Fulvio J. Vara, Chester; James A. Dougherty, Pequannock, both of N.J.; Jeffrey S. Plotkin, Monsey, N.Y.; Kolazi S. Narayanan, Palisades Park; Paul D. Taylor, West Milford, both of N.J.

[73] Assignee: ISP Investments Inc., Wilmington, Del.

[21] Appl. No.: 672,249

[22] Filed: Mar. 20, 1991

Related U.S. Application Data

[62] Division of Ser. No. 470,489, Jan. 26, 1990, Pat. No. 5,039,716.

[51] Int. Cl.$^5$ .................. B05D 3/06; B32B 27/16; B32B 31/28
[52] U.S. Cl. ..................... 428/428; 427/44; 427/54.1; 428/446; 428/450; 428/452
[58] Field of Search ............. 428/428, 446, 450, 452; 427/44, 54.1

[56] References Cited

U.S. PATENT DOCUMENTS 5,039,716 8/1991 Vara et al. .................. 522/96

Primary Examiner—James C. Cannon
Attorney, Agent, or Firm—Marilyn J. Maue; Joshua J. Ward

[57] ABSTRACT

Subject invention relates to alk-1-enyl ether silicates having the formula $$[X]_{4-n}Si[OR_1OCH=CH-R_2]_n$$

wherein X is halogen or —OR wherein R is lower alkyl or a mixture of halogen and OR, a mixture of OR and hydrogen or a mixture of halogen and hydrogen;

$R_1$ contains from 1 to 8 carbon atoms and is alkylene, alkenylene, alkynylene, optionally alkoxylated with up to 20 units of $$-(CH_2CHO)-\\ \phantom{-(CH_2C}|\\ \phantom{-(CH_2C}Y$$

wherein Y is hydrogen or methyl and $R_2$ is each hydrogen or lower alkyl and n has a value of from 1 to 4. The invention also relates to the process for preparing the above vinyl ether silicates and to their use as chemically resistant coatings.

9 Claims, No Drawings

ALK-1-ENYL ETHER SILICATES

This is a continuation of application Ser. No. 470,489, filed Jan. 26, 1990, now U.S. Pat. No. 5,039,716.

In one aspect, the invention relates to novel alk-1-enyl ether silicate compounds and in another aspect to their preparation and use.

BACKGROUND OF THE INVENTION

Certain radiation curable coatings and films such as those formed from the acrylates, particularly trimethylol propane triacrylate, trimethacrylate, pentaerythritol triacrylate, and hexanediol diacrylate or methacrylate, are in great demand because of their rapid curing properties. However, these compounds are normally highly viscous liquids or solids and thus are unsuitable as diluents for other polymeric components of a radiation curable formulation. Indeed, such compounds themselves require the incorporation of a diluent or solvent for uniform substrate coating, control of coating thickness and curing at low temperatures. Accordingly, low viscosity monofunctional diluents are usually included in their formulations. While these diluents are reactive, they materially reduce the cross-linked density of the finished product and consequently lower abrasion resistance and ability to withstand chemical attack.

Although solvents have been used to reduce viscosity, they are detrimental in radiation curing due to their volatility which presents problems for uniform composition control unless their evaporation prior to radiant exposure is effected. Obviously, such procedure extends processing time and may pose environmental drawbacks.

To some extent, the drawbacks of high viscosity monomers can be reduced by curing at elevated temperatures. However, this alternative significantly adds to the cost of the overall operation in the expenditure of energy, temperature control and loss of more volatile components in the composition or blistering of the coating resulting from entrained volatiles.

Since acrylate monomers are not conducive to cationically induced radiation curing, they require free radical systems which are oxygen inhibited unless effected in an inert atmosphere, generally under a blanket of nitrogen. Although formulation with a photoinitiator which undergoes bimolecular reaction with a hydrogen donor minimizes the inhibitory effect of air, this benefit is realized at the expense of a greatly reduced cure rate. Also, it is found that polymerization or curing in free radical systems ceases almost immediately upon removal from the source of radiation; thus, the cured product often contains significant amounts of unpolymerized components. Accordingly, it is an aim of research to develop a multifunctional monomer having the beneficial properties of multifunctional acrylates but which is amenable to radiation curing at a rapid rate by cationically induced polymerization which is not oxygen inhibited and which permits continued polymerization after removal from the source of radiation exposure.

A monomer having a functionality greater than 2 which is a low viscosity liquid and which can be polymerized cationically is greatly desired since such a monomer would allow greater control of the crosslink density of the cured product.

The inherent deficiencies of the acrylate systems can be partially overcome by the use of epoxy resins. Epoxy resins can be polymerized by normal radiation techniques using cationic photoinitiators such as iodonium, sulfonium and ferrocene salts of hexafluorophosphate, hexafluoroantimonate and hexafluoroarsonate to produce a tack free film. Although in such formulations tack free products are obtained, polymerization of the mixture is incomplete. It is well known that the polymerization of epoxy resins is extremely slow and requires as much as several days to achieve their ultimate physical properties. Thus, thermal post curing is often employed to increase the rate of or to complete the polymerization.

Certain allyl compounds also have been used as coatings; however these monomers and their oligomers are not readily curable by cationic radiation. Thermal curing is generally required to increase the rate of polymerization. While allyl ethers of polyethylene glycols are curable by UV light, they require a free radical initiated reaction which proceeds at a slow rate, generally over a period of from 2 to 10 hours in order to reach completion.

Finally, it is noted that the unsubstituted acrylates are sensitizers and skin irritants as well as being carcinogenic, so that specialized safety precautions must be taken to protect operators from exposure. Although alkoxylation has lessened irritancy of the acrylates, their carcinogenic properties are not reduced.

Accordingly it is an object of the present invention to overcome the above described deficiencies by an economical and commercially feasible composition and curing process.

Another object of this invention is to utilize a multifunctional cross-linking agent which is a liquid and which is more economically employed in an efficient cross-linking process.

Another object is to provide a non-toxic cross linkable homopolymeric compound suitable as a film or a substrate coating which possesses good adhesion, abrasion resistance and resistance to chemical attack.

Still another object is to provide a more economical process for cross-linking monomeric or polymeric vinyl or epoxy ethers which can be effected in the presence of air.

Another object is to provide a monomer which is curable at a rapid rate by cationically induced radiation.

These and other objects will become apparent from the following description and disclosure.

THE INVENTION

According to this invention there is provided an alk-1-enyl ether silicate having the formula $$[X]_{4-n}Si[OR_1OCH=CH-R_2]_n$$

wherein X is halogen, —OR wherein R is lower alkyl, a mixture of halogen and —OR, a mixture of —OR and hydrogen or a mixture of halogen and hydrogen;

$R_1$ contains from 1 to 8 carbon atoms and is alkylene, alkenylene, alkynylene, optionally alkoxylated with up to 20 units of

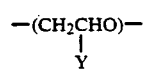

wherein Y is hydrogen or methyl, $R_2$ is hydrogen or lower alkyl and n has a value of from 1 to 4.

Of the above compounds, those mixtures wherein X contains —OR and wherein $R_2$ is hydrogen atoms, are preferred and products wherein n has a value of at least 2 are most preferred. Mixtures of the alk-1-enyl ether silicates of the present invention can contain varying amounts of 2 to 4 components where n has a value of 1,2,3 and/or 4. Preferred mixtures are those wherein the tris(vinyloxyalkylene) alkyl orthosilicate is present.

The products of this invention are prepared according to the reaction illustrated by the equation:

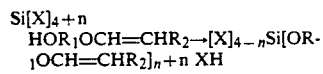
HOR$_1$OCH=CHR$_2$→[X]$_{4-n}$Si[OR$_1$OCH=CHR$_2$]$_n$+n XH silicate hydroxy alkenyl ether product by-product.

Suitable examples of silicate reactants include tetrachlorosilane, tetrafluorosilane, tetrabromosilane, tetramethyl orthosilicate, tetrabutyl orthosilicate, tetraethyl orthosilicate, tetrapropylyl orthosilicate, diethyl orthosilicate, dipropyl orthosilicate, tributyl orthosilicate, triethyl orthosilicate, tribromoethyl orthosilicate, dichlorodiethyl orthosilicate.

Representative hydroxy vinyl ethers which are suitably employed in the reaction include hydroxybutyl vinyl ether, hydroxyethyl vinyl ether, hydroxybutyl prop-1-enyl ether, hydroxyethyl but-1-enyl ether, hydroxyhexyl vinyl ether, hydroxyethyl 2-butyl hex-1-enyl ether, hydroxy butenyl vinyl ether, hydroxybutynyl vinyl ether, hydroxybutynyl-prop-1-enyl ether, hydroxypropynyl vinyl ether, hydroxybutyl 3-methyl-prop-1-enyl ether, the vinyl ether of di-hydroxymethyl cyclohexane and alkoxylated vinyl ether derivatives of the above having the formula

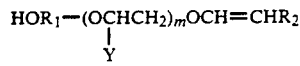

where m has a value of from 1 to 20, preferably from 1 to 8 and R$_1$, Y and R$_2$ are as defined above.

The mole ratio of silicate to hydroxylated alkenyl ether depends on the number of terminal alkenyl groups desired in the product and the number of halo and or OR groups in the silicate reactant and is as close to stoichiometry as is conveniently maintained; although up to a 10:1 excess of silicate reactant over said stoichiometric amount is within the scope of this invention.

The reaction is carried out under anhydrous conditions in the presence of from about 0.01 to about 10 wt. %, preferably from about 0.1 to about 5%, of a base catalyst based on the alkenyl ether reactant. Catalysts such as sodium or potassium metals, sodium or potassium hydroxides, hydrides, alkoxides or salts of the hydroxy alkenyl ether as well as titanium alkoxide are suitably employed. When halogenated silicates are employed, the addition of a base is required during the reaction to neutralize any hydrogen halide which is generated as by-product. Suitable bases include sodium hydroxide, potassium hydroxide, sodium or potassium alkoxides, pyridine or basic pyridine derivatives, ammonia and amines such as trimethyl amine, tripropylamine and the like.

The reaction mixture may also be affected in up to 90%, preferably not more than 50% suitable inert solvent such as toluene benzene, methyl ethyl ketone, N-methyl pyrrolidone, tetrahydrofuran, ethyl acetate, acetonitrile, and the like. Preferred inert solvents are those having a boiling point below that of the desired product.

Generally, the reaction is carried out at a temperature between about 50° and about 200° C. for a period of from about 5 to about 48 hours under from ambient pressure up to about 500 psi. Preferred reaction parameters include a temperature of between about 100° and about 120° C., a reaction time of from about 10 to 20 hours and a pressure from atmospheric to about 50 psi.

High conversion to product is achieved in the present reaction although a product mixture of mono and poly substituted silicates is usually obtained. Individual products can be separated by fractional distillation if desired. The crude product is separated from base catalyst by usual methods such as extraction and filtration, and from solvent, by evaporation under reduced pressure.

A major advantage of the present products is that they are rapidly curable at ambient temperatures by UV and visible light or other sources of radiation such as an electron beam, x-ray, laser emissions and the like. They are also reactive diluents for highly viscous coating materials, such as acrylates, vinyl ethers, epoxides, and non-reactive resins, etc., to promote rapid curing and strong bonding to substrate surfaces. From about 1 to about 60 wt. %, preferably from about 1 to about 30 wt. %, of the present alk-1-enyl ether silicates are added to said acrylates, epoxides and/or vinyl ethers to improve their curing properties.

The present products, in admixture or individually, can be applied to various substrates including metals, glass, ceramics, wood, paper and plastics and cured thereon to provide a strongly adhesive abrasion resistant surface which is water insoluble and which withstands chemical attack. Coatings of the present product can be applied up to 5 mil thickness by any conventional technique. When the substrate is paper, the present materials can contain a coloring agent and can be applied to the surface as an ink. These and many other uses of the present products, including use as highly reactive chemical intermediates, will become apparent from the foregoing disclosure.

Generally, UV light radiation dosages at room temperature of from about 100 to about 1500 millijoules/cm$^2$ are effective and dosages of from about 200 to about 600 millijoules/cm$^2$ are preferred. Equivalent dosages for curing are employed when using alternative sources of radiation. For example, curing with electron beam radiation can be carried out at between about 0.5 and about 20 Mrads, preferably between about 1 and about 10 Mrads. Specific techniques for radiation curing are well known, thus further amplification is not required. Coating mixtures involving the present compounds employ a suitable initiator, such as a free radical and cationic initiator mixture or a cationic photoinitiator e.g., an iodonium, sulfonium or ferrocene salt or mixtures thereof, a mixture of aromatic complex salts in butyrolactone (e.g. FX-512, supplied by Minnesota Mining & Mfg. Co.), an aromatic complex salt of hexafluorophosphate, hexafluoroantimonate, or hexafluoroarsonate, and hydroxycyclohexyl phenyl ketone (IRGACURE 184, supplied by Ciba-Geigy), 2-hydroxy-2-methyl-1-phenyl-1-propan-1-one (DAROCUR 1173), 2,2-dichloro-1-(4-phenoxyphenyl)ethanone (SANDORAY 1000) and the like. Other free radical and cationic initiators which are suitably employed in this invention are those described by M. J. M. Abadie, Advantages and Development of Photochemical Initiators, in the European Coatings Journal 5/1988, pages 350-358. The initiator in the composition is present in an amount, between about 0.1 and about 10 wt. %, preferably between about 0.5 and about 5 wt. % of which at least 25% is a cationic initiator.

When the silicate compounds of this invention are used as a diluent in a polymerizable composition containing from about 30 to about 99 wt. %, preferably from about 40 to about 60 wt. %, of a vinyl ether, epoxy ether, vinyloxy alkyl urethane or oligomer thereof or bisphenol A epoxyacrylate oligomer, the composition can be cured at a rapid rate with an initiator containing between about 25 and 100% of a cationic initiator; although mixtures of a cationic initiator and from about 20 to about 75% of a free radical initiator are also beneficially employed and, in fact, are recommended when the polymerizable compound is an epoxy acrylate monomer or oligomer.

The use of a surfactant which is inert with respect to the alk-1-enyl ether silicate is also beneficially employed in the composition. Fluorochemical surfactants e.g. a mixture of fluoroaliphatic polymeric esters (e.g. FC-430 supplied by Minnesota Mining & Mfg. Co.) in a concentration of from about 0.05 to about 5 parts/100 parts of resin have been found to be useful.

Having generally described the invention, reference is now had to the accompanying examples which illustrate preferred embodiments but which are not to be construed as limiting to the scope of the invention as more broadly described above and in the appended claims.

EXAMPLE I

A one liter round bottomed flask, equipped with a magnetic stirrer, thermometer, water condenser and dry ice trap attached to vacuum, was charged with 438 g. (3.78 moles) of hydroxybutyl vinyl ether, 196 g. (0.94 mole) of tetraethylorothosilicate and 5 g. of KOH pellets. The flask was heated to 55°-60° C. for 4 hours, during which time 40 g. of ethanol by-product was taken off. The vacuum was then removed and nitrogen gas was introduced. The flask was then heated to 110° C. under ambient pressure. After 12 hours an additional 78 g. of ethanol by-product was removed.

A. The crude reaction product (463 g.) was flash distilled. The main fraction (292 g.) distilling at 100°-200° C. under 3 mm Hg was found to contain 85% tris (vinyl oxybutyl) ethyl orthosilicate and 15% bis (vinyl oxybutyl) ethyl orthosilicate.

B. A separate 50 g. portion of the crude reaction product was flash distilled at 210° C., 1 mm Hg. Analysis of 47 g. of the clear, colorless distillate was identified as 81.2% tris (vinyl oxybutyl) ethyl orthosilicate, 15.2% bis (vinyl oxybutyl) diethyl orthosilicate and 0.8% tetra (vinyl oxybutyl) orthosilicate.

EXAMPLE II

A 3-necked 100 ml round bottomed flask, equipped with a magnetic stirrer, vertical water condenser connected to vacuum via a trap and nitrogen gas inlet was charged with 25 g. of the above main fraction (Example IA), 40 g. of hydroxybutyl vinyl ether and 0.5 g. of KOH. The flask was heated to 100° C. under a blanket of nitrogen for a period of 5 hours after which the mixture was flash distilled, unreacted material removed at 100° C. under 3 mm Hg and the remaining distillate collected. The collected distillate was found to be a mixture of 87% tris (vinyl oxybutyl ethyl) orthosilicate and 10% tetra (vinyl oxybutyl ethyl) orthosilicate.

EXAMPLE III

The main fraction of Example I (Part A) was mixed with an equal weight amount of the diglycidyl ether of bisphenol A (EPON-828, Shell), 1 part per hundred parts of resin of a fluorochemical surfactant (FC-430), and 4 parts per hundred parts of resin of a cationic photoinitiator FX-512 at 50° C. until a homogeneous low viscosity liquid was obtained. This mixture was then coated on an aluminum substrate at a thickness of 1.2 mil. The coated surface was exposed for less than 1 second to 400 millijoules/cm$^2$ from a mercury vapor lamp. A tack free, film was produced. Coating properties reported in the following table were determined immediately after UV exposure and after a post cure at 177° C. for 15 minutes.

TABLE

| Property | After UV Exposure | After Post Cure |
|---|---|---|
| Pencil Hardness (ASTM D 3363) | <4B | F |
| % Adhesion (ASTM D 3359) | 0 | 80 |
| Double MEK Rubs | 39 | >100 |
| Reverse Impact | — | <10 |
| Mandrel Bend (in.) (ASTM D 3111) | ⅛ | ⅛ |

EXAMPLE IV

The mixture described in Example III was coated on a polyester substrate at a thickness of 0.5 mil. The coated surface was exposed to 400 millijoules/cm$_2$ UV light for less than 1 second and post cured for 2 hours at 50° C. Chemical resistance was tested by the covered spot test (ASTM D 1308). No attack was observed after 24 hours exposure to 1% H$_2$SO$_4$, 1% NaOH, 10% acetic acid, or distilled water.

EXAMPLE V

The mixture described in Example III was coated on an aluminum panel at a thickness of 0.25 mil. The coated surface was exposed to an electron beam dosage of 3 Mrads for less than 1 second to produce a tack free film. Coating properties reported in the following Table were determined immediately after electron beam exposure and after a post cure at 150° C. for 15 minutes.

TABLE

| Property | After EB | Post Cured |
|---|---|---|
| Pencil Hardness | HB | H |
| % Adhesion | 100 | 100 |
| MEK Double Rubs | 2 | 18 |
| Mandrel Bend | ⅛ | ⅛ |

EXAMPLE VI

The main fraction of Example I part A (25.0 gm) was mixed with the divinyl ether of triethylene glycol (25.0 gm) a bisphenol A epoxy acrylate oligomer (EBECRYL-3700, Radcure Specialties, 50.0 gm), 2 phr* cationic photoinitiator (FX 512), 2 phr* free radical photoinitiator (IRGACURE-184) and 1 phr* fluorochemical surfactant (FC-430) at 50° C. until a homogeneous low viscosity liquid was obtained. This mixture was then coated on a polyester substrate at a thickness of 0.5 mil.
*parts/100 parts resin
The coated surface was exposed to 400 millijoules/cm$^2$ from a mercury vapor lamp for less than 1 second. A tack free coating with the following properties was produced.

| | |
|---|---|
| Pencil Hardness | 2H |
| Adhesion | 100% |
| Double MEK Rubs | >100 |

EXAMPLE VII

The main fraction from Example I part A (6.20 gm) was mixed with the divinyl ether of triethylene glycol (18.8 gm) and a divinyl ether urethane oligomer (prepared as described in the Degree Thesis of Lennart Carlsson, Dept. of Polymer Technology, The Royal Institute of Technology, Stockholm Sweden, 1987; 25.0 gm); 4 phr cationic photoinitiator (FX-512), and 1 phr fluorochemical surfactant (FC-430) at 50° C. until a homogeneous low viscosity liquid was obtained. This mixture was then coated on a aluminum panel (0.25 mil) and exposed to 400 millijoules/cm² from a mercury vapor lamp for less than 1 second. A tack free coating with the following properties was produced

| | |
|---|---|
| Pencil Hardness | 3B |
| Mandrel Bend | 3/16 inch |
| Double MEK Rubs | 11 |

What is claimed is:

1. A substrate having a cured surface coating of the alk-1-enyl ether silicate having the formula $$[X]_{4-n}Si[OR_1OCH=CH-R_2]_n$$

wherein X is halogen, —OR where R is lower alkyl, a mixture of halogen and —OR, a mixture of —OR and hydrogen or a mixture of hydrogen and halogen; $R_1$ contains from 1 to 8 carbon atoms and is alkylene, alkenylene, alkynylene optionally alkoxylated with up to 20 units of $$-(CH_2CHO)-\underset{Y}{|}$$

where Y is hydrogen or methyl; $R_2$ is hydrogen or lower alkyl and n has a value of from 1 to 4.

2. The substrate of claim 1 having a coating which is a mixture of poly(vinyloxy lower alkyl) orthosilicates.

3. The substrate of claim 2 wherein said mixture contains $$Si[OR_1OCH=CH-R_2]_4$$

4. The substrate of claim 2 which contains (vinyl oxybutyl) ethyl orthosilicates.

5. The substrate of claim 4 wherein the (vinyl oxybutyl) ethyl orthosilicates contain tris(vinyl oxybutyl) ethyl orthosilicate.

6. The process which comprises forming a mixture containing a vinyl ether, epoxide or acrylate resin, a cure enhancing amount of the alk-1-enyl ether silicate of claim 1 and an effective cure promoting amount of a cationic photoinitiator; coating the resulting mixture on a substrate and curing said mixture by exposure to a source of radiation for a period sufficient to provide a tack free coating on said substrate.

7. The process of claim 6 wherein between about 5 and about 75 wt. % of said alk-1-enyl ether silicate is added to said resin.

8. The process of claim 7 wherein said alk-1-enyl ether silicate is a mixture of about 80% tris(vinyl oxybutyl) ethyl orthosilicate and about 15% bis(vinyl oxybutyl) ethyl orthosilicate.

9. The process of claim 6 wherein said mixture is exposed to said source of radiation in less than one second.

* * * * *